United States Patent [19]

Winn

[11] E Re. 29,196

[45] Reissued Apr. 26, 1977

[54] ALKYLPHENYL BENZOPYRANOPYRIDINES

[75] Inventor: Martin Winn, Deerfield, Ill.

[73] Assignee: Abbott Laboratories, North Chicago, Ill.

[22] Filed: June 25, 1976

[21] Appl. No.: 699,831

Related U.S. Patent Documents

Reissue of:

[64] Patent No.: 3,932,432
Issued: Jan. 13, 1976
Appl. No.: 442,032
Filed: Feb. 13, 1974

U.S. Applications:

[63] Continuation-in-part of Ser. No. 345,942, April 2, 1973, abandoned.

[52] U.S. Cl. ..... 424/256; 260/240 D; 260/270 E; 260/295 T; 260/297 T

[51] Int. Cl.[2] ..... A61K 31/44; C07D 491/04

[58] Field of Search ..... 260/297 T, 295 T, 270 E; 424/256

[56] References Cited

UNITED STATES PATENTS 3,878,219 4/1975 Lee ..... 260/295 T

*Primary Examiner*—Alan L. Rotman

*Attorney, Agent, or Firm*—Robert L. Niblack; Joyce R. Niblack

[57] ABSTRACT

Alkylphenyl benzopyranopyridines represented by the formula

I where $R_1$ is hydrogen, loweralkyl, loweralkanoyl, cycloalkylloweralkyl, cycloalkylloweralkanoyl, loweralkenyl, loweralkynyl, halologweralkenyl, phenylloweralkyl, phenylloweralkenyl or phenylloweralkynyl; $R_2$ is loweralkyl; $R_3$ is hydrogen; Y is a straight or branched chain alkylene group having from one to ten carbon atoms; and each $R_4$ and $R_5$ and $R_6$ are the same or different members of the group consisting of hydrogen, halo, trifluoromethyl or loweralkyl; and the pharmaceutically acceptable salts thereof.

16 Claims, No Drawings

ALKYLPHENYL BENZOPYRANOPYRIDINES

Matter enclosed in heavy brackets [ ] appears in the original patent but forms no part of this reissue specification; matter printed in italics indicates the additions made by reissue.

REFERENCE TO RELATED APPLICATION

This application is a continuation-in-part of copending application filed Apr. 2, 1973, bearing Ser. No. 345,942, now abandoned.

DETAILED DESCRIPTION OF THE INVENTION

This invention relates to novel alkylphenyl benzopyranopyridines and to heterocyclic esters thereof, to methods of preparing the compounds, to pharmaceutical compositions containing the compounds and to use of the compounds and pharmaceutical compositions containing the compounds for pharmacological and medicinal purposes.

According to one aspect of this invention, compounds are provided which can be represented by the formula

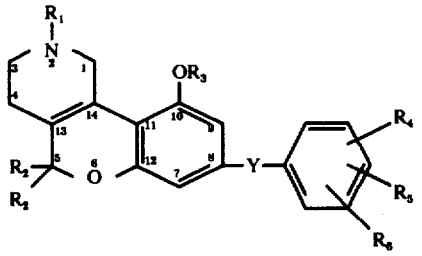

wherein $R_1$ is hydrogen, loweralkyl, loweralkanoyl, cycloalkylloweralkyl, cycloalkylloweralkanoyl, loweralkenyl, loweralkynyl, halo loweralkenyl, phenylloweralkyl, phenylloweralkenyl or phenylloweralkynyl; $R_2$ is loweralkyl; $R_3$ is hydrogen; Y is a straight or branched chain alkylene group having from one to ten carbon atoms; and each $R_4$ and $R_5$ and $R_6$ are the same or different members of the group consisting of hydrogen, halo, trifluoromethyl or loweralkyl; and the pharmaceutically acceptable salts thereof.

The term "loweralkyl" as used herein, refers to $C_1$–$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The term "loweralkenyl" refers to straight and branched chain $C_2$–$C_6$ alkyl radicals from which a hydrogen atom has been removed from each of two adjacent carbon atoms to produce ethylenic unsaturation; e.g., vinyl, allyl, methallyl, 1-pentenyl and the like.

The term "loweralkynyl" refers to $C_2$–$C_6$ alkyl groups as defined above, from which two hydrogen atoms have been removed from each of two adjacent carbon atoms to produce acetylenic unsaturation; e.g., ethynyl, propargyl, 2-butynyl, 1-pentynyl and the like groups.

The term "halo" includes chloro, fluoro, bromo and iodo.

The term "loweralkanoyl" refers to saturated monovalent, aliphatic radicals derived from a monocarboxylic acid, including straight or branched chain radicals of from one to six carbon atoms including the formyl, acetyl, propionyl, α-methylpropionyl, butyryl, hexanoyl and the like radicals.

"Cycloalkyl," as used herein, refers to cyclic saturated aliphatic radicals having three to eight carbon atoms in a ring, such as cyclopropyl, cyclobutyl, cyclopentyl, cyclohexyl, cycloheptyl and cyclooctyl.

"Cycloalkylloweralkyl" refers to groups such as cyclopropyl-methyl, 2-methylcyclobutyl and the like.

The term "pharmaceutically acceptable salts" refers to salts such as sodium, potassium, calcium, barium, aluminum, ammonium and substituted ammonium salts, such as methyl ammonium, benzyl ammonium, triethanol ammonium salts and the like. Such salts are well known in the art and are considered to be "pharmaceutically acceptable."

Generally speaking, the preferred compounds of this invention wherein $R_3$ is hydrogen can be prepared by the following routes:

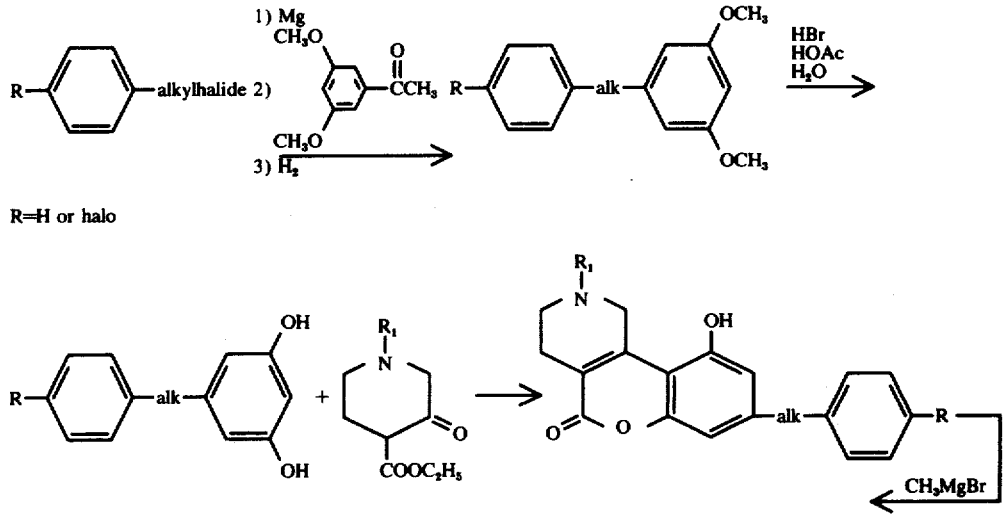

-continued
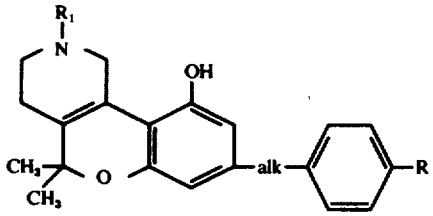
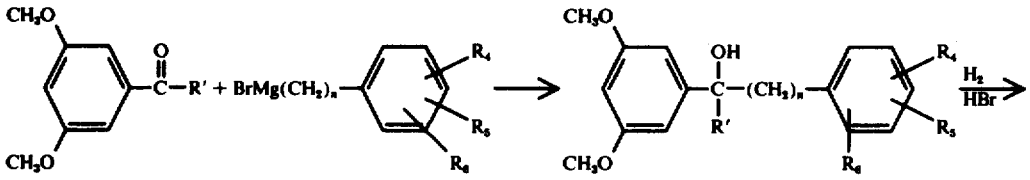
(R = Alkyl)
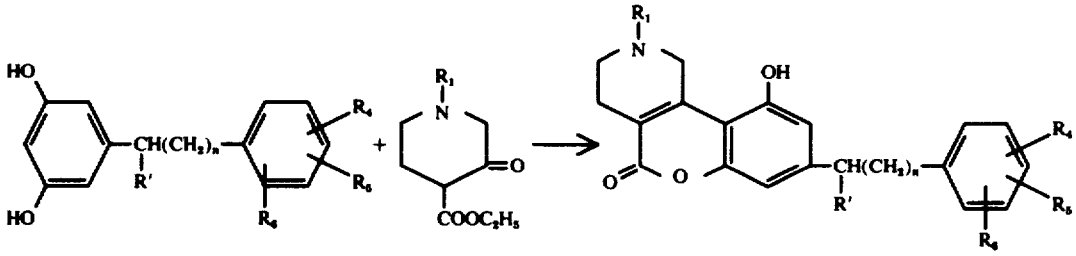
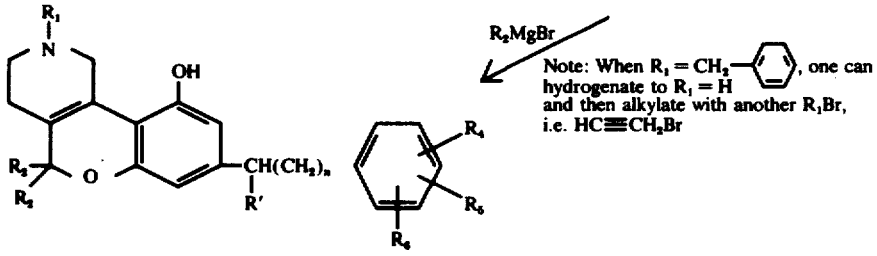
Note: When $R_1 = CH_2$—⬡, one can hydrogenate to $R_1 = H$ and then alkylate with another $R_1Br$, i.e. $HC{\equiv}CH_2Br$
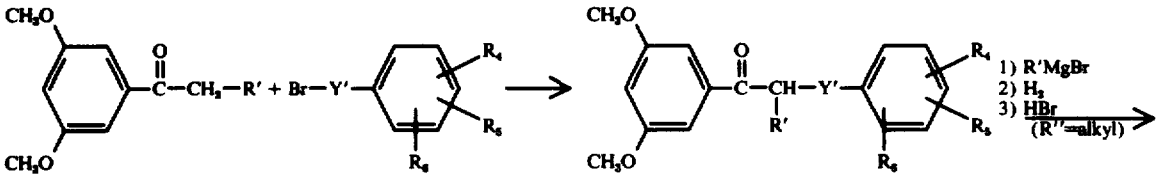
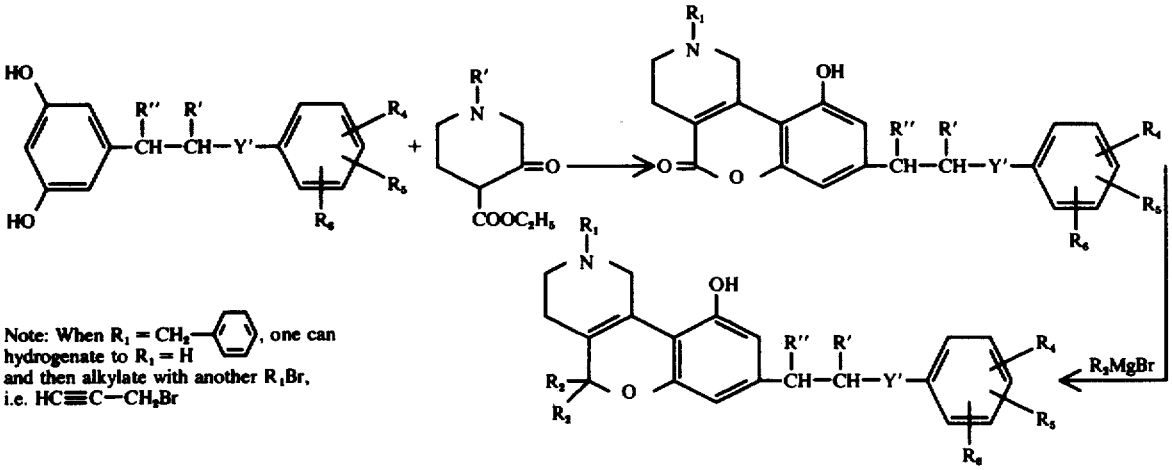
Note: When $R_1 = CH_2$—⬡, one can hydrogenate to $R_1 = H$ and then alkylate with another $R_1Br$, i.e. $HC{\equiv}C{-}CH_2Br$ -continued

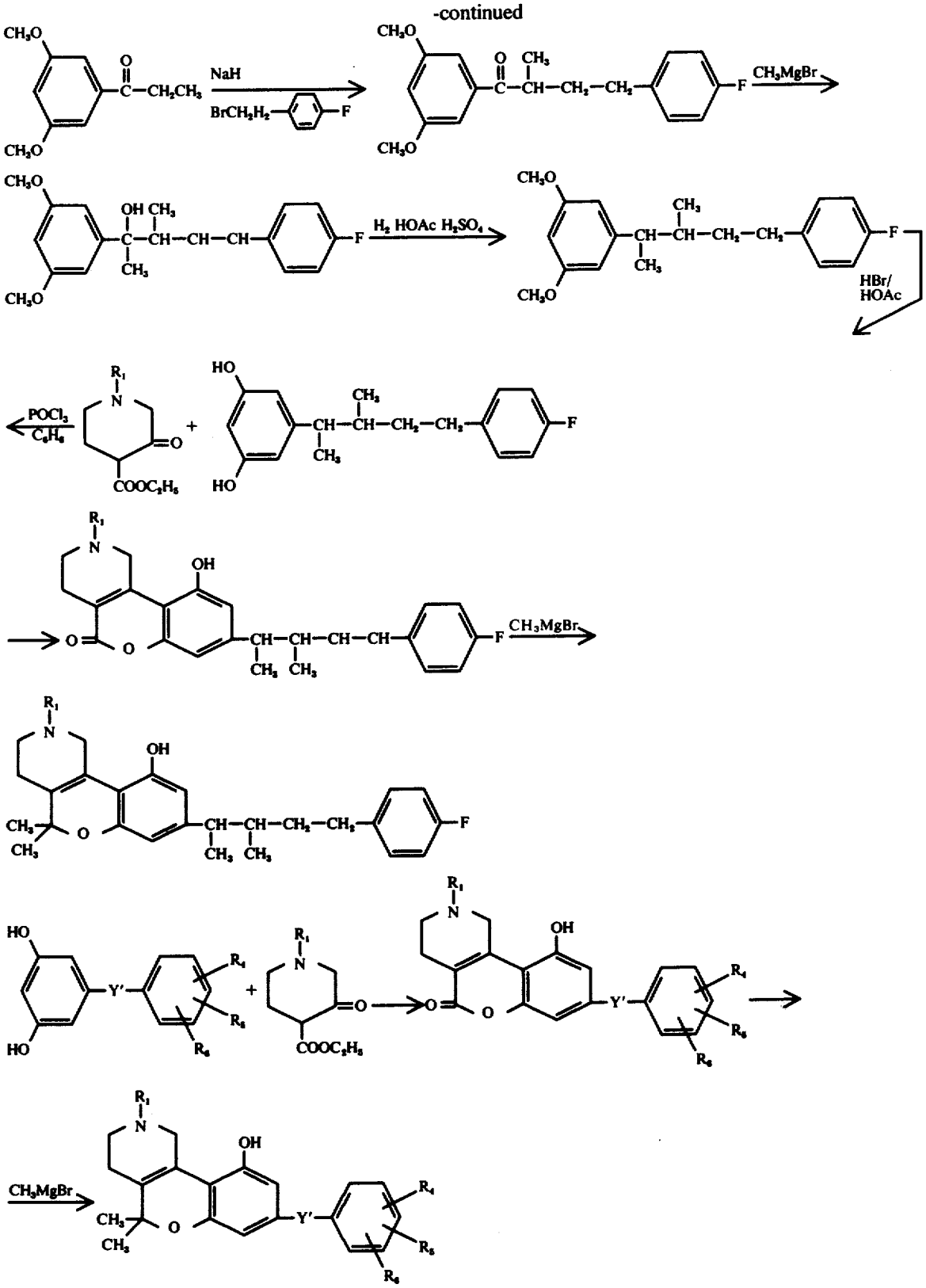

The compounds of this invention are useful as analgesic agents at dosages of from 0.01 – 25.0 mg./kg. of body weight daily. The presently preferred compound, [ 5,5-dimethyl-8-(4-p-fluorophenyl-1-methylbutyl)-10-hydroxy-2-(2-propynyl)-1,2,3,4-tetrahydro-5H[1]benzopyrano[4,3-c]pyridin-10-ol ] *5,5-dimethyl-8-[4-(p-fluorophenyl)-1-methylbutyl]-10-hydroxy-2-(2-propynyl)-1,2,3,4-tetrahydro-5H[1]benzopyrano[4,3-c]pyridine* has an oral $ED_{50}$ of 5.3 mg./kg. in the mouse writhing test for analgesia, [Whittle, Brit.

J. Pharmacol., 22, 296 (1964)], (codeine has an oral $ED_{50}$ of 15.6 mg./kg. in the mouse writhing test); an oral $ED_{50}$ of 3.7 mg./kg. in the rat tail flick test [Harris, et al. J. Pharm. Exp. Ther. 169 17 (1969)], and an oral $ED_{50}$ of 5.7 mg./kg. in the hot plate test.

In addition to their use as analgesic agents, the compounds are useful as mild tranquilizers at dosages of from 0.01 – 20 mg./kg. of body weight daily. Since many patients suffering from pain are anxious and apprehensive, the compounds of this invention are particularly useful as analgesic agents. The compounds further appear to produce analgesia and mild tranquilization without sedative or sedative-hypnotic effect, thus enabling the patients to carry out their normal activities while taking a compound of this invention.

In addition to their use as analgesics and tranquilizers, the compounds are also useful as anticonvulsants, antidiarrheals and antiulcer agents. They may be administered via oral, parenteral or intravenous administration.

The present invention includes within its scope pharmaceutical compositions comprising, as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate and sweetening and flavoring agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents and sweeting, flavoring and perfuming agents.

Preparations according to this invention for parenteral administration include sterile aqueous or nonaqueous solutions, suspensions or emulsions. Examples of nonaqueous solvents or vehicles are propylene glycol, polyethylene glycol, vegetable oils, such as olive oil, and injectable organic esters such as ethyl oleate. Such dosage forms may also contain adjuvants such as preserving wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment. Generally, dosage levels of between 0.01 – 25 mg./kg. of body weight daily are administered to patients in need of analgesia or tranquilization or for other needs stated above.

The following example further illustrates the pharmaceutical compositions which are a feature of this invention:

EXAMPLE 1

Tablets weighing 200 mg. and having the following composition are prepared by standard tableting procedures:

| Ingredient | Mg. |
|---|---|
| [Preparation of 5,5-Dimethyl-8-(4-p-fluorophenyl-1-methyl-butyl)-10-hydroxy-2-(2-propynyl)-1,2,3,4-tetrahydro-5H[1]benzopyranal[4,3-c]pyridine-10-ol] | |
| *5,5-Dimethyl-8-[4-(p-fluorophenyl)-1-methylbutyl]-10-hydroxy-2-(2-propynyl)-1,2,3,4-tetrahydro-5H[1]benzopyrano[4,3-c]pyridine* | 100 |
| starch | 94 |
| colloidal silica | 5 |
| magnesium stearate | 1 |

It will be understood by those skilled in the art that the above composition can contain any of the compounds of this invention.

The following examples further illustrate this invention without, however, limiting it thereto:

EXAMPLE 2

Preparation of 2-(3,5-Dimethoxyphenyl)-5-(p-Fluorophenyl)Pentane

A solution of 77 g. of 3-(p-fluorophenyl)propylbromide in 300 ml. of ether was added dropwise over a two-hour period to a refluxing solution of 10 g. of magnesium in 100 ml. of ether. The reaction mixture was refluxed for an additional 30 minutes after the addition was completed. A solution of 68 g. of 3,5-dimethoxyacetophenone in 100 ml. of ether was then added dropwise to the reaction and the mixture was refluxed for 1½ hours. To the reaction was added 300 ml. of a saturated ammonium chloride solution dropwise with stirring. The layers were separated and the aqueous layer extracted with ether. The ether extract was dried over magnesium sulfate and the ether removed in vacuo to give an oil. An additional 111.7 g. of 3-(p-fluorophenyl)propylbromide was reacted with 3,5-dimethoxyacetophenone in the above manner. The products from both runs were hydrogenated in ethanol-HCl using palladium as the catalyst. The solvents and catalyst were removed and the crude material distilled to yield 169.0 g. of 2-(3,5-dimethoxyphenyl)-5-(p-fluorophenyl)pentane, b.p. 145 – 155/0.05 mmHg.

Analysis Calcd. for $C_{19}H_{23}O_2F$: C, 75.60; H, 7.69 Found: C, 75.87; H, 7.98

EXAMPLE 3

Preparation of 2-(3,5-Dihydroxyphenyl)-5-(p-Fluorophenyl)Pentane

Fifty grams of the above-prepared 2-(3,5-dimethoxyphenyl)-5-(p-fluorophenyl)pentane, 450 ml. of acetic acid and 180 ml. of 48% HBr in water were mixed. While cooling, the mixture was saturated with hydrogen gas (approximately one-half hour). The reaction was placed in an 87° bath and stirred for 17 hours. The reaction was then concentrated in vacuo and the residue neutralized with $K_2CO_3$ and $NaHCO_3$, extracted with ether, treated with charcoal and $MgSO_4$ and filtered to yield 45 g. of 2-(3,5-dihydroxyphenyl)-5-(p-fluorophenyl)pentane as a brown oil which distills at 180°/0.01 mmHg.

Analysis Calcd. for $C_{17}H_{19}O_2F$: C, 74.20; H, 6.98 Found: C, 73.56; H, 7.04

EXAMPLE 4

Preparation of

[ 2-Benzyl-8-(4-p-Fluorophenyl-1-Methylbutyl)-10-Hydroxy-5-Oxo-1,2,3,4-Tetrahydro-5H-[1]Benzopyrano[4,3-c]Pyridin-10-ol Hydrochloride]

*2-Benzyl-8-[4-(p-fluorophenyl)-1-methylbutyl]-10-hydroxy-5-oxo-1,2,3,4-tetrahydro-5H[1]benzopyrano[4,3-c]pyridine hydrochloride*

To 45 g. of 2-(3,5-dihydroxyphenyl)-5-(4-fluorophenyl)pentane dissolved in 100 ml. of methanesulfonic acid were added in portions, 57 g. of 1-benzyl-3-keto-4-carbethoxy piperidine hydrochloride. While stirring, 68 g. of $POCl_3$ was added and the solution was stirred for 5 days at room temperature. Water (300 ml.) and 180 ml. of $CHCl_3$ were then added and the reaction mixture stirred for 30 minutes. After the addition of 100 ml. of 15% NaOH, the reaction was stirred for an additional 10 minutes. The $CHCl_3$ layer was separated and extracted with 10% HCl. The $CHCl_3$ layer was concentrated and $CH_3CN$ added thereto to yield 55 g. of the desired product as the hydrochloride salt, m.p. 254° – 256° C.

Theory: C, 70.80; H, 6.14; Cl, 6.97; N, 2.75 Found: C, 70.15; H, 6.17; Cl, 7.23; N, 2.74

EXAMPLE 5

Preparation of

[ 2-Benzyl-5,5-Dimethyl-8-(4-Fluorophenyl-1-Methylbutyl)-10-Hydroxy-1,2,3,4-Tetrahydro-5H[1]Benzopyrano[4,3c]Pyridin-10-ol ]

*2-Benzyl-5,5-dimethyl-8-[4-(p-fluorophenyl)-1-methylbutyl]-10-hydroxy-1,2,3,4-tetrahydro-5H[1]benzopyrano[4,3-c]pyridine*

Sixty-five grams of the above-prepared [ 2-benzyl-8-(4-fluorophenyl-1-methylbutyl)-10-hydroxy-5-oxo-1,2,3,4-tetrahydro-5H-[1]benzopyrano[4,3-c]pyridin-10-ol hydrochloride ] *2-benzyl-8-[4-(p-fluorophenyl)-1-methylbutyl]-10-hydroxy-5-oxo-1,2,3,4-tetrahydro-5H[1]benzopyrano[4,3-c]pyridine hydrochloride* were suspended in 300 ml. of $CHCl_3$. After adding a $KHCO_3$ solution, the reaction was stirred for 30 minutes. The chloroform layer was separated, dried over $MgSO_4$, concentrated, taken up in benzene and concentrated again. The concentrate was taken up in 185 ml. of hot anisole and the resulting solution was added dropwise to a solution of $CH_3MgBr$ in anisole (prepared by adding 180 g. of $CH_3Br$ in 500 ml. of ether to 40 g. of Mg in 150 ml. of ether, evaporating the ether and adding 300 ml. of anisole). The reaction mixture was stored overnight at 62° C. Water (200 ml.) was added slowly, followed by 400 ml. of 10% $H_2SO_4$. The anisole was removed by steam distillation and the resulting solid was taken up in chloroform, neutralized with $KHCO_3$, dried over $MgSO_4$, concentrated and the product (36.6 g.), m.p. 188° – 190° C., crystallized from $CH_3CN$.

Analysis Calcd. for $C_{32}H_{36}FNO_2$: C, 79.15; H, 7.47; N, 2.89 Found: C, 78.86; H, 7.67; N, 2.79

EXAMPLE 6

Preparation of

[ 5,5-Dimethyl-8-(4-p-Fluorophenyl-1-Methylbutyl)-10-Hydroxy-1,2,3,4-Tetrahydro-5H[1]Benzopyrano[4,3-c]Pyridin-10-ol Hydrochloride ]

*5,5-Dimethyl-8-[4-(p-fluorophenyl)-1-methylbutyl]-10-hydroxy-1,2,3,4-tetrahydro-5H[1]benzopyrano[4,3-c]pyridine hydrochloride*

32.8 g. of the above-prepared [ 2-benzyl-5,5-dimethyl-8-(4-fluorophenyl-1-methylbutyl)-10-hydroxy-1,2,3,4-tetrahydro-5H[1]benzopyrano[4,3-c]pyridin-10-ol] *2-benzyl-5,5;dimethyl-8-[4-(p-fluorophenyl)-1-methylbutyl]-10-hydroxy-1,2,3,4-tetrahydro-5H[1]benzopyrano[4,3-c]pyridine* hydrochloride (m.p. 231 – 235, prepared by reacting the base of Example 5 with HCl in ethanol and crystallizing from ethyl acetate) was hydrogenated in ethanol. The catalyst was removed, the solution concentrated, and the desired product was crystallized from ethanol-Skelly B as 19.9 g. of amorphous solid, m.p. 222° – 225° C.

Theory: C, 69.50; H, 7.23; N, 3.24; Cl, 8.21 Found: C, 69.67; H, 7.34; N, 3.12; Cl, 8.10

EXAMPLE 7

Preparation of

[ 5,5-Dimethyl-8-(4-p-Fluorophenyl-1-Methylbutyl)-10-Hydroxy-2-(2-Propynl)-1,2,3,4-Tetrahydro-5H[1]Benzopyrano[4,3-c]Pyridin-10-ol ]

*5,5-Dimethyl-8-[4-(p-fluorophenyl)-1-methylbutyl]-10-hydroxy-2-(2-propynyl)-1,2,3,4-tetrahydro-5H[1]benzopyrano[4,3-c]pyridine*

[ 5,5-Dimethyl-3-(4-p-fluorophenyl-1-methylbutyl)-10-hydroxy-1,2,3,4-tetrahydro-5H[1]benzopyrano[4,3-c]pyridin-10-ol ] *5,5-Dimethyl-8-[4-(p-fluorophenyl)-1-methylbutyl]-10-hydroxy-1,2,3,4-tetrahydro-5H[1]benzopyrano[4,3-c]pyridine* as the free base (19.9 g.) was dissolved in 88 ml. of dimethylformamide. While the solution was cooling, 3.14 g. of propargyl bromide was added. The reaction was stirred at room temperature for 15 hours. Water (120 ml.) was added slowly, whereupon the desired product crystallized. The crystalline product was washed with water and recrystallized from ether and $CH_3CN$ to yield 5.90 g. of the desired product, m.p. 164° – 166° C.

Analysis Calcd. for $C_{28}H_{32}FNO_2$: C, 77.25; H, 7.46; N, 3.21 Found: C, 77.57; H, 7.76; N, 3.11

EXAMPLE 8

2-(3,5-Dimethoxyphenyl)-5-(4-Methylphenyl)Pentane

By the method described in Example 2, 3([4-] p-methylphenyl)propyl bromide was converted into the desired product b.p. 170–175/0.6mm.

Analysis Calcd. for $C_{20}H_{26}O_2$: C, 80.49; H, 8.78 Found: C, 80.31; H, 9.14

EXAMPLE 9

[ 2-Benzyl-8-(4-p-Methylphenyl-1-Methylbutyl)-10-Hydroxy-5-Oxo-1,2,3,4-Tetrahydro-5H[1]Benzopyrano[4,3-c]Pyridin-10-ol Hydrochloride]

*2-Benzyl-8-[4-(p-methylphenyl)-1-methylbutyl]-10-hydroxy-5-oxo-1,2,3,4-tetrahydro-5H[1]benzopyrano[4,3-c]pyridine hydrochloride*

The compound of Example 8 was converted to the resorcinol by the method described in Example 3 and the resulting resorcinol converted to the desired compound by the method of Example 4. The product had m.p. 236° – 240° C.

Analysis Calcd. for $C_{31}H_{34}ClNO_3$: C, 73.95; H, 6.81; N, 2.78 Found: C, 73.80; H, 6.81; N, 280

EXAMPLE 10

[ 2-Benzyl-5,5-Dimethyl-8-(4-p-Methylphenyl-1-Methylbutyl)-10-Hydroxy-1,2,3,4-Tetrahydro-5H[1]Benzopyrano[4,3-c]Pyridin-10-ol Hydrochloride ]

*2-Benzyl-5,5-dimethyl-8-[4-(p-methylphenyl)-1-methylbutyl]-10-hydroxy-1,2,3,4-tetrahydro-5H[1]benzopyrano[4,3-c]pyridine hydrochloride*

The compound of Example 9 was converted to the desired compound by the method of Example 5. The base was converted to the hydrochloride with HCl in ethanol. Product had m.p. 225° – 226° C.

Analysis Calcd. for $C_{33}H_{40}ClNO_2$: C, 82.20; H, 8.16; N, 2.91 Found: C, 81.87; H, 8.44; N, 2.79

EXAMPLE 11

[ 5,5-Dimethyl-8-(4-p-Methylphenyl-1-Methylbutyl)-10-Hydroxy-2-(2-Propynyl)-1,2,3,4-Tetrahydro-5H[1]Benzopyrano[4,3-c]Pyridin-10-ol ]

*5,5-Dimethyl-8-[4-(p-methylphenyl)-1-methylbutyl-10-hydroxy-2-(2-propynyl)-1,2,3,4-tetrahydro-5H[1]benzopyrano[4,3-c]pyridine*

The compound of Example 10 was hydrogenated as described in Example 6 and alkylated with propargyl bromide as described in Example 7. The desired product had m.p. 159° – 160° C.

Analysis Calcd. for $C_{29}H_{35}NO_2$: C, 81.08; H, 8.21; N, 3.26 Found: C, 81.39; H, 8.47; N, 3.31

EXAMPLE 12

2(3,5-Dimethoxyphenyl-4-(4-Fluorophenyl)Butane

By the method described in Example 2, 2( [4-] p-fluorophenyl)ethyl bromide was converted to the desired compound b.p. 145 – 155/0.3.

Analysis Calcd. for $C_{18}H_{21}FO_2$: C, 75.01; H, 7.34 Found: C, 75.09; H, 7.54

EXAMPLE 13

[ 2-Benzyl-8-(3-p-Fluorophenyl-1-Methylpropyl)-10-Hydroxy-5-Oxo-1,2,3,4-Tetrahydro-5H[1]Benzopyrano[4,3-c]Pyridin-10-ol Hydrochloride ]

*2-Benzyl-8-[3-(p-fluorophenyl)-1-methylpropyl]-10-hydroxy-5-oxo-1,2,3,4-tetrahydro-5H[1]benzopyrano[4,3-c]pyridine hydrochloride*

The compound of Example 12 was converted into the resorcinol by the method of Example 3 and the resulting resorcinol converted into the desired compound by the method of Example 4. The product had m.p. 243° – 246° C.

Analysis Calcd. for $C_{29}H_{29}ClFNO_3$: C, 70.91; H, 5.91; N, 2.83 Found: C, 71.14; H, 6.04 N, 2.77

EXAMPLE 14

[ 2-Benzyl-5,5-Dimethyl-8-(3-p-Fluorophenyl-1-Methylpropyl)-10-Hydroxy-1,2,3,4-Tetrahydro-5H[1]Benzopyrano[4,3-c]Pyridin-10-ol Hydrochloride ]

*2-Benzyl-5,5-dimethyl-8-[3-(p-fluorophenyl)-1-methylpropyl]-10-hydroxy-1,2,3,4-tetrahydro-5H[1]benzopyrano[4,3-c]pyridine hydrochloride*

The compound of Example 13 was converted to the desired compound by the method of Example 5. The base was converted to the hydrochloride with HCl in ethanol. The product had m.p. 237° – 270° C.

Analysis Calcd. for $C_{31}H_{35}ClFNO_2$: C, 78.80; H, 7.26; N, 2.97 Found: C, 78.45; H, 7.44; N, 2.78

EXAMPLE 15

[ 5,5-Dimethyl-8-(3-p-Fluorophenyl-1-Methylpropyl)-10-Hydroxy-2-(2-Propynyl)-1,2,3,4-Tetrahydro-5H[1]Benzopyrano[4,3-c]Pyridin-10-ol ]

*5,5-Dimethyl-8-[3-(p-fluorophenyl)-1-methylpropyl]-10-hydroxy-2-(2-propynyl)-1,2,3,4-tetrahydro-5H[1]benzopyrano[4,3-c]pyridine*

The compound of Example 14 was hydrogenated as described in Example 6 and alkylated with propargyl bromide as described in Example 7. The desired product had m.p. 174° – 175° C.

Analysis Calcd. for $C_{27}H_{30}FNO_2$: C, 77.25; H, 7.20; N, 3.33 Found: C, 77.30; H, 7.12; N, 3.17

EXAMPLE 16

2(3,5-Dimethoxyphenyl)-6-(4-Fluorophenyl)Hexane

By the method described in Example 2, 4-(4-fluorophenyl)butyl chloride was converted into the desired product b.p. 155 – 160/0.3mm.

Analysis Calcd. for $C_{20}H_{25}FO_2$: C, 75.95; H, 7.96 Found: C, 76.24; H, 7.93

EXAMPLE 17

[ 2-Benzyl-8-(5-p-Fluorophenyl-1-Methylpentyl)-10-Hydroxy-5-Oxo-1,2,3,4-Tetrahydro-5H[1]Benzopyrano[4,3-c]Pyridin-10-ol Hydrochloride ]

*2-Benzyl-8-[5-(p-fluorophenyl)-1-Methylpentyl]-10-hydroxy-5-oxo-1,2,3,4-tetrahydro-5H[1]benzopyrano[4,3-c]pyridine hydrochloride*

The compound of Example 16 was converted to the resorcinol by the method described in Example 3 and the resulting resorcinol converted to the desired product by the method of Example 4. The product had m.p. 227° – 228° C.

Analysis Calcd. for $C_{31}H_{33}ClFNO_3$: C, 71.32; H, 6.37 N, 2.68 Found; C, 71.05 H, 6.38 N, 2.76

EXAMPLE 18

[ 2-Benzyl-5,5-Dimethyl-8-(5-p-Fluorophenyl-1-Methylpentyl)-10-Hydroxy-1,2,3,4-Tetrahydro-5H[1]Benzopyrano[4,3-c]Pyridin-10-ol Hydrochloride ]

*2-Benzyl-5,5-dimethyl-8-[5-(p-fluorophenyl)-1-methylpentyl]-10-hydroxy-1,2,3,4-tetrahydro-5H[1]benzopyrano[4,3-c]pyridine hydrochloride*

The compound of Example 13 was converted to the desired compound by the method of Example 5. The base was converted to the hydrochloride with HCl in ethanol. The product had m.p. 208° – 210° C.

Analysis Calcd. for $C_{33}H_{39}ClFNO_2$: C, 73.93; H, 7.33 N, 2.61 Found: C, 73.68 H, 7.48 N, 2.62

EXAMPLE 19

[ 5,5-Dimethyl-8-(5-p-Fluorophenyl-1-Methylpentyl)-10-Hydroxy-2-(2-Propynyl)-1,2,3,4-Tetrahydro-5H[1]Benzopyrano[4,3-c]Pyridin-10-ol ]

*5,5-Dimethyl-8-[5-(p-fluorophenyl)-1-methylpentyl]-10-hydroxy-2-(2-propynyl)-1,2,3,4-tetrahydro-5H[1]benzopyrano[4,3-c]pyridine*

The compound of Example 18 was hydrogenated as described in Example 6 and alkylated with propargyl bromide as described in Example 7. The desired product had m.p. 146° – 147° C.

Analysis Calcd. for $C_{29}H_{31}FNO_2$: C, 77.82; H, 7.65; N, 3.12 Found: C, 77.20; H, 7.59; N, 3.06

EXAMPLE 20

2(3,5-Dimethoxyphenyl)-3-Methyl-5-(p-Fluorophenyl)Pentane 3,5-Dimethoxy propiophenone (52.0 g.) was added to a suspension prepared from 13.9 g. 57% sodium hydride in mineral oil (which had been freed of mineral oil by washing with toluene) and 130 ml. toluene. The resulting mixture was refluxed 30 minutes, 51 g. of 2(p-fluorophenyl)ethyl bromide added and refluxed 2-$Y_2$. The mixture was worked up with water and HCl and the product distilled to give 66.4 g. 1-(3,5-dimethoxyphenyl)-2-methyl-4(p-fluorophenyl)-1-butanone b.p. 160 – 175/0.3mm. This ketone in 300 ml. ether was treated with 130 ml. of 3 molar methyl magnesium bromide in ether and worked up with ammonium chloride to give 71.0 g. 2(3,5-dimethoxyphenyl)-3-methyl-5(p-fluorophenyl)-2-pentanol. This alcohol was hydrogenated in acetic acid containing 2 ml. $H_2SO_4$ using palladium catalyst to give 55.0 g. of desired compound b.p. 150 – 155/0.3mm. Gas chromatography showed 2 isomers of ratio 63/37.

Analysis Calcd. for $C_{20}H_{25}FO_2$: C, 75.95; H, 7.96 Found: C, 76.04; H, 8.22

EXAMPLE 21

[ 2-Benzyl-8-(4-p-Fluorophenyl-1,2-Dimethylbutyl)-10-Hydroxy-5-Oxo-1,2,3,4-Tetrahydro-5H[1]Benzopyrano[4,3-c]Pyridin-10-ol Hydrochloride ]

*2-Benzyl-8-[4-(p-fluorophenyl)-1,2-dimethylbutyl]-10-hydroxy-5-oxo-1,2,3,4-tetrahydro-5H[1]benzopyrano[4,3-c]pyridine hydrochloride*

The compound of Example 20 was converted to the resorcinol by the method described in Example 3 and the resulting resorcinol converted to the desired compound by the method of Example 4. The product had m.p. 252° – 258° C.

Analysis Calcd. for $C_{31}H_{33}ClFNO_3$: C, 71.20 H, 6.47 N, 2.68 Found: C, 71.12 H, 6.56 N, 2.95

EXAMPLE 22

[ 2-Benzyl-5,5-Dimethyl-8-(4-p-Fluorophenyl-1,2-Dimethylbutyl)-10-Hydroxy-1,2,3,4-Tetrahydro-5H[1]Benzopyrano[4,3-c]Pyridin-10-ol Hydrochloride ]

*2-Benzyl-5,5-dimethyl-8-[4-(p-fluorophenyl)-1,2-dimethylbutyl]-10-hydroxy-1,2,3,4-tetrahydro-5H[1]benzopyrano[4,3-c]pyridine hydrochloride*

The compound of Example 21 was converted to the desired compound by the method of Example 5. The base had m.p. 201° – 204° C. The base was converted to the hydrochloride by HCl in ethanol. The hydrochloride had m.p. 223° – 225° C.

Analysis for base $C_{33}H_{38}FNO_2$: C, 69.25; H, 7.66; N, 2.80 Found: C, 79.18; H, 7.64; N, 2.77

EXAMPLE 23

[ 5,5-Dimethyl-8-(4-p-Fluorophenyl-1,2-Dimethylbutyl)-10-Hydroxy-2-(2-Propynyl)-1,2,3,4-Tetrahydro-5H[1]Benzopyrano[4,3-c]Pyridin-10-ol ]

*5,5-Dimethyl-8-[4-(p-fluorophenyl)-1,2-dimethylbutyl]-10-hydroxy-2-(2-propynyl)-1,2,3,4-tetrahydro-5H[1]benzopyrano[4,3-c]pyridine*

The compound of Example 22 was hydrogenated as described in Example 6 and alkylated with propargyl bromide as described in Example 7. The desired product had m.p. 174° – 177° C.

Analysis Calcd. for $C_{29}H_{34}FNO_2$: C, 77.85; H, 7.66; N, 3.13 Found: C, 77.94; H, 7.89; N, 3.12

EXAMPLE 24

2-(3,5-Dimethoxyphenyl)-3-Methyl-6-(4-Fluorophenyl)Hexane 3,5-Dimethoxy propiophenone, 3(4-fluorophenyl)-propyl bromide and methyl magnesium bromide were used to prepare the desired compound as described in Example 20. The product had b.p. 170 – 180/0.5mm. Gas chromatography showed 2 isomers in a 62/38 ratio.

EXAMPLE 25

[ 2-Benzyl-8-(5-p-Fluorophenyl-1,2-Dimethylpentyl)-10-Hydroxy-5-Oxo-1,2,3,4-Tetrahydro-5H[1]Benzopyrano[4,3-c]Pyridin-10-ol of Hydrochloride ]

*2-Benzyl-8-[5-(p-fluorophenyl)-1,2-dimethylpentyl]-10-hydroxy-5-oxo-1,2,3,4-tetrahydro-5H[1]benzopyrano[4,3-c]pyridine hydrochloride*

The compound of Example 24 was converted to the resorcinol by the method described in Example 3 and the resulting resorcinol converted to the desired compound by the method of Example 4. The product had m.p. 222° – 224° C.

EXAMPLE 26

[ 2-Benzyl-5,5-Dimethyl-8-(5-p-Fluorophenyl-1,2-Dimethylpentyl)-10-Hydroxy-1,2,3,4-Tetrahydro-5H[1]Benzopyrano[4,3-c]Pyridin-10-ol Hydrochloride ]

*2-Benzyl-5,5-dimethyl-8-[5-(p-fluorophenyl)-1,2-dimethylpentyl]-10-hydroxy-1,2,3,4-tetrahydro-5H[1]benzopyrano[4,3-c]pyridine hydrochloride*

The compound of Example 25 was converted to the desired compound by the method of Example 5. The base was converted to the hydrochloride by HCl in ethanol. The product had m.p. 217° – 218° C.

Analysis Calcd. for $C_{34}H_{41}ClFNO_2$: C, 74.22; H, 7.51; N, 2.54 Found: C, 73.69; H, 7.44; N, 2.55

EXAMPLE 27

[ 5,5-Dimethyl-8-(5-p-Fluorophenyl-1,2-Dimethylpentyl)-10-Hydroxy-2-(2-Propynyl)-1,2,3,4-Tetrahydro-5H[1]Benzopyrano[4,3-c]Pyridin-10-ol ]

*5,5-Dimethyl-8-[5-(p-fluorophenyl)-1,2-dimethylpentyl]-10-hydroxy-2-(2-propynyl)-1,2,3,4-tetrahydro-5H[1]benzopyrano[4,3-c]pyridine*

The compound of Example 26 was hydrogenated as described in Example 6 and alkylated with propargyl bromide as described in Example 7. The desired product had m.p. 155° – 156° C.

Analysis Calcd. for $C_{30}H_{36}FNO_2$: C, 78.05; H, 7.86; N, 3.03 Found: C, 78.19; H, 8.00; N, 3.04

EXAMPLE 28

[ 5,5-Dimethyl-8-[4(4-Chloro-3-Trifluoromethylphenyl)-1-Methylbutyl]-10-Hydroxy-2-(2-Propynyl)-1,2,3,4-Tetrahydro-5H[1]Benzopyrano[4,3-c]Pyridin-10-ol ]

*8-[4-(4-Chloro-3-trifluoromethylphenyl)-1-methylbutyl]-5,5-dimethyl-10-hydroxy-2-(2-propynyl)-1,2,3,4-tetrahydro-5H[1]benzopyrano[4,3-c]pyridine*

4-Chloro-3-trifluoromethyl aniline was converted to the diazonium salt with sodium nitrite and sulfuric acid and this was reacted with acrylic acid (Meerwein reaction) to give 4-chloro-3-trifluoromethyl cinnamic acid. This acid was hydrogenated, reduced with lithium aluminum hydride to the alcohol and reacted with phosphorus tribromide to give 3(4-chloro-3-trifluoromethylphenyl)propyl bromide.

The above bromide was converted to 2(3,5-dihydroxyphenyl)-5-(4-chloro-3-trifluoromethylphenyl)-pentane by the method described in Examples 2 and 3, and this in turn was converted into the final product by reaction with 1-benzyl-3-keto-4-carbethoxy piperidine as described in Example 4 followed by methyl magnesium bromide (as in Example 5), hydrogen (as in Example 6) and propargyl bromide (as in Example 7).

EXAMPLE 29

[ 5,5-Dimethyl-8-[4(2-Chloro-4-Methylphenyl)-1-Methylbutyl]-10-Hydroxy-2-(2-Propynyl)-1,2,3,4-Tetrahydro-5H[1]Benzopyrano[4,3-c]Pyridin-10-ol ]

*8-[4-(2-Chloro-4-methylphenyl)-1-methylbutyl]-5,5-dimethyl-10-hydroxy-2-(2-propynyl)-1,2,3,4-tetrahydro-5H[1]benzopyrano[4,3-c]pyridine*

Starting with 2-chloro-4-methylaniline the reaction sequence of Example 28 was followed yielding the desired product.

EXAMPLE 30

[ 5,5-Dimethyl-8-(4-p-Fluorophenyl-1-Methylbutyl)-10-Hydroxy-2-(3-Methyl-2-Butenyl)-1,2,3,4-Tetrahydro-5H[1]Benzopyrano[4,3-c]Pyridin-10-ol ]

5-5-Dimethyl-8-(4-p-Fluorophenyl-1-Methylbutyl)-10-Hydroxy-2-(3-Chloro-2-Propenyl)-1,2,3,4-Tetrahydro-5H[1]Benzopyrano[4,3-c]Pyridin-10-ol

[5,5-Dimethyl-8-(4-p-fluorophenyl-1-methylbutyl)-10-hydroxy-1,2,3,4-tetrahydro-5H[1]benzopyrano[4,3-c]pyridin-10-ol] *5,5-Dimethyl-8-[4-(p-fluorophenyl)-1-methylbutyl]-10-hydroxy-1,2,3,4-tetrahydro-5H[1]benzopyrano[4,3-c]pyridine* (1 mole) and 1-bromo-3-methylbutene-2 (0.5 mole) were reacted in dimethyl formamide as described in Example 7 to give the desired product.

EXAMPLE 31

[5,5-Dimethyl-8-(4-p-Fluorophenyl-1-Methylbutyl)-10-Hydroxy-2-(3-Chloro-2-Propenyl)-1,2,3,4-Tetrahydro-5H[1]Benzopyrano[4,3-c]Pyridin-10-ol ]

*5,5-Dimethyl-8-[4-(p-fluorophenyl)-1-methylbutyl]-10-hydroxy-2-(3-chloro-2-propenyl)-1,2,3,4-tetrahydro-5H[1]benzopyrano[4,3-c]pyridine*

[ 5,5-Dimethyl-8-(4-p-fluorophenyl-1-methylbutyl)-10-hydroxy-1,2,3,4-tetrahydro-5H[1]benzopyrano[4,3-c]pyridin-10-ol ] *5,5-Dimethyl-8-[4-(p-fluorophenyl)-1-methylbutyl]-10-hydroxy-1,2,3,4-tetrahydro-5H[1]benzopyrano[4,3-c]pyridine* (1 mole) and 1,3-dichloro-2-butene (0.5 mole) were reacted in dimethylformamide as described in Example 7 to give the desired product.

EXAMPLE 32

[ 5,5-Dimethyl-8-(4-p-Fluorophenyl-1-Methylbutyl)-10-Hydroxy-2-(Cyclopropylmethyl)-1,2,3,4-Tetrahydro-5H[1]Benzopyrano[4,3-c]Pyridin-10-ol ]

*5,5-Dimethyl-8-[4-(p-fluorophenyl)-1-methylbutyl]-10-hydroxy-2-cyclopropylmethyl-1,2,3,4-tetrahydro-5H[1]benzopyrano[4,3-c]pyridine*

[ 5,5-Dimethyl-8-(4-p-fluorophenyl-1-methylbutyl)-10-hydroxy-1,2,3,4-tetrahydro-5H[1]benzopyrano[4,3-c]pyridin-10-ol ] *5,5-Dimethyl-8-[4-(p-fluorophenyl)-1-methylbutyl]-10-hydroxy-1,2,3,4-tetrahydro-5H[1]benzopyrano[4,3-c]pyridine* (1 mole) and cyclopropylmethylbromide were reacted in dimethylformamide as described in Example 7 to give the desired product.

EXAMPLE 33

[5,5-Dimethyl-8-(4-p-Fluorophenyl-1-Methylbutyl)-2-Propyl-10-Hydroxy-1,2,3,4-Tetrahydro-5H[1]Benzopyrano[4,3-c]Pyridin-10-ol ]

*5,5-Dimethyl-8-[4-(p-fluorophenyl)-1-methylbutyl]-2-propyl-10-hydroxy-1,2,3,4-tetrahydro-5H[1]benzopyrano[4,3-c]pyridine*

[ 5,5-Dimethyl-8-(4-p-fluorophenyl-1-methylbutyl)-2-(2-propynyl)-10-hydroxy-1,2,3,4-tetrahydro-5H[1]benzopyrano[4,3-c]pyridin-10-ol ] *5,5-Dimethyl-8-[4-(p-fluorophenyl)-1-methylbutyl]-10-hydroxy-2-(2-propynyl)-1,2,3,4-tetrahydro-5H[1]benzopyrano[4,3-c]pyridine* was hydrogenated in ethanol using 5% palladium on carbon as a catalyst. When two equivalents of hydrogen were taken up, the catalyst was filtered and solution concentrated to give the desired product.

EXAMPLE 34

[ 5,5-Dimethyl-8-(4-p-Fluorophenyl-1-Methylbutyl)-2-[3(3,4,5-Trimethoxyphenyl)-2-Propenyl]-10-Hydroxy-1,2,3,4-Tetrahydro-5H[1]Benzopyrano[4,3-c]Pyridin-10-ol ] *5,5-Dimethyl-8-[4-(p-fluorophenyl)-1-methylbutyl]-2-[3-(3,4,5-trimethoxyphenyl)-2-propenyl]-10-hydroxy-1,2,3,4-tetrahydro-5H[1]benzopyrano[4,3-c]pyridine*

[ 5,5-Dimethyl-8-(4-p-fluorophenyl-1-methylbutyl)-10-hydroxy-1,2,3,4-tetrahydro-5H[1]benzopyrano[4,3-c]pyridin-10-ol ] *5,5-Dimethyl-8-[4-(p-fluorophenyl)-1-methylbutyl]-10-hydroxy-1,2,3,4-tetrahydro-5H[1]benzopyrano[4,3-c]pyridine* (1 mole) and 1-(3-chloropropenyl)3,4,5-trimethoxybenzene and (0.5 mole) were reacted in dimethylformamide as described in Example 7 to give the desired product.

EXAMPLE 35

[ 5,5-Dimethyl-8-(4-p-Fluorophenyl-1-Methylbutyl)-2-(Cyclobutanecarbonyl)-10-Hydroxy-1,2,3,4-Tetrahydro-5H[1]benzopyrano[4,3-c]Pyridin-10-ol ]

*2-Cyclobutanecarbonyl-5,5-dimethyl-8-[4-(p-fluorophenyl)-1-methylbutyl]-10-hydroxy-1,2,3,4-tetrahydro-5H[1]benzopyrano[4,3-c]pyridine*

[ 5,5-Dimethyl-8-(4-p-fluorophenyl-1-methylbutyl)-10-hydroxy-1,2,3,4-tetrahydro-5H[1]benzopyrano[4,3-c]pyridin-10-ol ] *5,5-Dimethyl-8-[4-(p-fluorophenyl)-1-methylbutyl]-10-hydroxy-1,2,3,4-tetrahydro-5H[1]benzopyrano[4,3-c]pyridine* (1 mole) and cyclobutanecarbonyl chloride (1 mole) with triethylamine (1 mole) in dimethylformamide, stirring 16 hours at 25° C gave the desired product.

I claim:

1. A compound of the formula

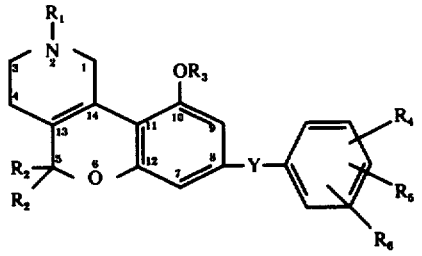

where $R_1$ is hydrogen, loweralkyl, 3-methyl-2-butenyl, *propargyl*, 3-chloro-2-propenyl, cyclopropylmethyl, phenylloweralkyl, or 3(3,4,5-trimethoxyphenyl)-2-propenyl; $R_2$ is methyl; $R_3$ is hydrogen; [ Y is a radical of the formula

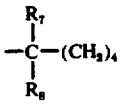

where n is a linear chain of 1–9 carbon atoms and $R_7$ is H or $CH_3$; ]

*Y is a straight or branched chain alkylene group having 4 to 7 carbon atoms and having no branch larger than a methyl group;* and each $R_4$ and $R_5$ and $R_6$ are the same or different members of the group consisting of hydrogen, halo, trifluoromethyl or loweralkyl; and the pharmaceutically acceptable salts thereof.

2. A compound in accordance with claim 1 wherein $R_1$ is benzyl.

3. A compound in accordance with claim 1 wherein $R_1$ is hydrogen.

4. A compound in accordance with claim 1 wherein $R_1$ is propargyl [ and each $R_2$ is methyl ].

5. A compound in accordance with claim 1 of the formula

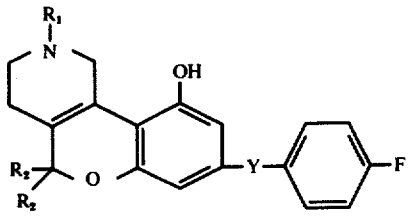

where $R_1$ is hydrogen, loweralkyl, 3-methyl-2-butenyl, *2-propynyl*, 3-chloro-2-propenyl, cyclopropylmethyl, phenylloweralkyl, or 3(3,4,5-trimethoxyphenyl)-2-propenyl; $R_2$ is methyl, Y is a radical of the formula

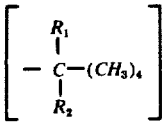

[ where n is a linear chain of 1–9 carbon atoms and $R_7$ is H or $CH_3$. ]

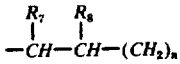

*where n is an integer from 1 to 3 inclusive, $R_7$ is hydrogen or methyl and $R_8$ is hydrogen or methyl except that $R_8$ cannot be methyl if $R_7$ is hydrogen.*

[ 6. A compound in accordance with claim 5, 2-benzyl-5,5-dimethyl-3-(4-fluorophenyl-1-methylbutyl)-10-hydroxy-1,2,3,4-tetrahydro-5H[1]benzopyrano[4,3-c]pyridin-10-ol. ]

[ 7. A compound in accordance with claim 5, 5,5-dimethyl-3-(4-fluorophenyl-1-methylbutyl)-10-hydroxy-1,2,3,4-tetrahydro-5H[1]benzopyrano[4,3-c]pyridin-10-ol hydrochloride. ]

[ 8. A compound in accordance with claim 5, 5,5-dimethyl-3-(4-fluorophenyl-1-methylbutyl)-10-hydroxy-2-[2-propynyl)]-1,2,3,4-tetrahydro-5H[1]benzopyrano[4,3-c]pyridin-10-ol. ]

*9. 2-Benzyl-5,5-dimethyl-8-[4-(p-fluorophenyl)-1-methylbutyl]-10-hydroxy-1,2,3,4-tetrahydro-5H[1]benzopyrano[4,3-c]pyridine.*

*10. 5,5-Dimethyl-8-[4-(p-fluorophenyl)-1-methylbutyl]-10-hydroxy-1,2,3,4-tetrahydro-5H[1]benzopyrano[4,3-c]pyridine hydrochloride.*

*11. 5,5-Dimethyl-8-[4-(p-fluorophenyl)-1-methylbutyl]-10-hydroxy-2-(2-propynyl)-1,2,3,4-tetrahydro-5H[1]benzopyrano[4,3-c]pyridine.*

*12. A compound of the formula*

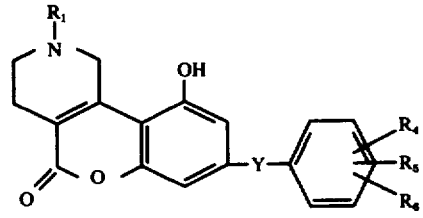

*wherein $R_1$ is hydrogen, $C_1$–$C_6$ alkyl, $C_2$–$C_6$ alkenyl, $C_2$–$C_6$ alkynyl, halo($C_2$–$C_6$)alkenyl, halo ($C_2$–$C_6$) alkynyl*

*or phenyl ($C_1$–$C_6$) alkyl; Y is a straight or branched chain alkylene group having from 4 to 7 carbon atoms and having no branch larger than a methyl group; and each $R_4$ and $R_5$ and $R_6$ are the same or different members of the group consisting of hydrogen, halo, trifluoromethyl or loweralkyl.*

*13. A compound in accordance with claim 12 of the formula*

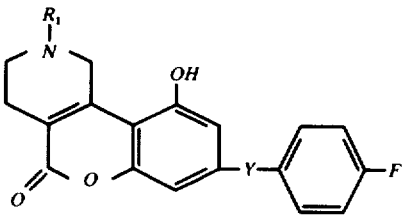

*wherein Y is a radical of the formula*

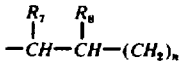

*where n is an integer from 1 to 3 inclusive, $R_7$ is hydrogen or methyl and $R_8$ is hydrogen or methyl except that $R_8$ cannot be methyl when $R_7$ is hydrogen.*

*14. A compound in accordance with claim 13, 2-Benzyl-8[4-(p-fluorophenyl)-1-methylbutyl]-10-hydroxy-5-oxo-1,2,3,4-tetrahydro-5H[1]benzopyrano[4,3-c]pyridine.*

*15. A compound in accordance with claim 13, 8-[4-(p-fluorophenyl)-1-methylbutyl]-10-hydroxy-5-oxo-1,2,3,4-tetrahydro-5H[1]benzopyrano[4,3-c]pyridine.*

*16. A pharmaceutical composition in unit dosage form comprising an analgesic effective amount of a compound of claim 1 and a pharmaceutically acceptable carrier or diluent.*

*17. A pharmaceutical composition in accordance with claim 16 wherein said compound is 5,5-Dimethyl-8-[4-(p-fluorophenyl)-1-methylbutyl]-10-hydroxy-2-(2-propynyl)-1,2,3,4-tetrahydro-5H[1]benzopyrano[4,3-c]pyridine.*

*18. A method of relieving pain comprising administering a therapeutically effective amount of a compound of claim 1 to a patient in need of such treatment.*

*19. The method of claim 18 wherein the compound is 5,5-dimethyl-8-[4-(p-fluorophenyl)-1-methylbutyl]-10-hydroxy-2-(2-propynyl)-1,2,3,4-tetrahydro-5H[1]benzopyrano[4,3-c]pyridine.*

* * * * *